United States Patent [19]
Perusek

[11] Patent Number: 6,059,784
[45] Date of Patent: May 9, 2000

[54] CAPACITIVE EXTENSOMETER PARTICULARLY SUITED FOR MEASURING IN VIVO BONE STRAIN

[75] Inventor: Gail P. Perusek, Lakewood, Ohio

[73] Assignee: The United States of America as represented by the Administrator of the National Aeronautics and Space Administration, Washington, D.C.

[21] Appl. No.: 09/179,355

[22] Filed: Oct. 8, 1998

[51] Int. Cl.[7] .................................................. A61B 17/56
[52] U.S. Cl. .............................................. 606/54; 606/102
[58] Field of Search .............................. 606/54, 102, 57, 606/59

[56] References Cited

U.S. PATENT DOCUMENTS

| | | |
|---|---|---|
| 3,577,883 | 5/1971 | Werner . |
| 3,995,696 | 12/1976 | Kainer et al. . |
| 4,141,349 | 2/1979 | Ory et al. . |
| 4,160,325 | 7/1979 | DeNicola . |
| 4,251,918 | 2/1981 | Duggan . |
| 4,576,158 | 3/1986 | Boland ................................... 606/102 |
| 4,607,531 | 8/1986 | Meline et al. . |
| 4,628,583 | 12/1986 | Barnett . |
| 4,939,445 | 7/1990 | Meline et al. . |
| 4,964,862 | 10/1990 | Arms ....................................... 606/102 |
| 5,289,826 | 3/1994 | Kovacevic .............................. 606/102 |
| 5,334,202 | 8/1994 | Carter ..................................... 606/102 |
| 5,360,016 | 11/1994 | Kovacevic .............................. 606/102 |
| 5,402,684 | 4/1995 | Engeler et al. . |
| 5,425,775 | 6/1995 | Kovacevic et al. ..................... 606/102 |
| 5,456,724 | 10/1995 | Yen et al. . |
| 5,695,496 | 12/1997 | Orsak et al. . |
| 5,919,192 | 7/1999 | Shouts ..................................... 606/102 |

OTHER PUBLICATIONS

C.T. Rubin et al,"Regulation of Bone Mass by Mechanical Strain Magnitude," published in Calcified Tissue International, 1985, 37:411–417.
S.C. Corwin, "Posture Load–Induced Bone Maintenance—A New Hypothesis," published in NASA–funded Project #199–26–17–04 in 1997.
G.D. Whedon, "Disuse Osteoporis: Physiological Aspects," published in Calcified Tissue International in 1984, 36, S146–S150.
P.C. Rambaut et al, "Skeletal Response," published in 1975 in Biomedical Results of Apollo, prepared by R.S. Johnson et al, Document SP–377—Washintong, D.C., pp. 303–322.
M.C. Michel et al, "Compressive Fatigue Behavior of Bovine Trabecular Bone," published in 1993—J. Biomechanics 26:453–463.
C. Milgrom et al, "A Comparison of the Effect of Shoe Gear on Human Tibial Axial Strains Measured In Vivo" Abstract from ORS 43rd Annual Mtg., Feb. 1997.

Primary Examiner—Michael Buiz
Assistant Examiner—Daphna Shai
Attorney, Agent, or Firm—Kent N. Stone

[57] ABSTRACT

The present invention provides for in vivo measurements of the principal strain magnitudes and directions, and maximum shear strain that occurs in a material, such as human bone, when it is loaded (or subjected to a load). In one embodiment the invention includes a capacitive delta extensometer arranged with six sensors in a three piece configuration, with each sensor of each pair spaced apart from each other by 120 degrees.

7 Claims, 14 Drawing Sheets

FIG-2
(SECTION 2-2)

FIG-10
(SECTION 10-10)

CAPACITIVE EXTENSOMETER PARTICULARLY SUITED FOR MEASURING IN VIVO BONE STRAIN

ORIGIN OF THE INVENTION

The invention described herein was made by an employee of the United States Government, and may be manufactured and used by or for the Government for governmental purposes without the payment of any royalties thereon or therefor.

FIELD OF THE INVENTION

This invention relates to a extensometer for measuring the strain in a specimen. More particularly, the present invention relates to measuring the in vivo bone strain of a mammal. Specifically, the present invention relates to an extensometer, and a method of operation thereof, that measures the principal strain magnitudes and directions, and maximum shear strain that occurs within bones of a human when subjected to strain.

BACKGROUND OF THE INVENTION

The ability of bone to form optimal structures to support loads and adapt structurally to changing loads is termed the "strain-adaptive remodeling response." The exact nature of the mechanical remodeling signal, or osteogenic stimulus, is not fully understood. However, several mechanical parameters have been proposed, including strain magnitude, frequency, and rate. It is thought that 1 to 2 Hz events during locomotion produce levels of strain on the order of 1000 to 3000 microstrain (or 0.1 to 0.3%), and are osteogenic in nature. These 1 to 2 Hz events are more fully described by Rubin C T and Lanyon L E, in the 1985 technical article "Regulation of Bone Mass by Mechanical Strain Magnitude," published in *Calcified Tissue International*, 37:411–417, which is herein incorporated by reference.

Further, it has been proposed that higher frequency events (15 to 25 Hz) of lower magnitude (100 to 250 microstrain), possibly associated with muscular contractions to maintain posture, are of importance in maintaining bone mass. These 15 to 25 Hz events are more fully described by Cowin, S C, in the 1997 report "Posture Load-Induced Bone Maintenance—A New Hypothesis" disclosed in NASA-funded Project #199-26-17-04, which is herein incorporated by reference. Removing this stimulus in environments such as those encountered during space flight will inhibit the process of bone deposition. It is well documented that bone loss is a physiologic effect of space flight. For example, this bone loss is more fully described by Rambaut P C, Smith M C Jr., Mack P B, Vogel J M, in the 1975 report "Skeletal Response" published in *Biomedical Results of Apollo* prepared by R S. Johnson, L. F. Dietlein, and C. A. Berry (eds.), (Document SP-377). Washington, D.C., pp. 303–322, which is herein incorporated by reference. In addition, this bone loss is also more fully described by Whedon, G. D., in the 1984 technical article "Disuse Osteoporosis: Physiological Aspects," published in *Calcified Tissue International*, 36, S146–S150, which is herein incorporated by reference. Thus, the accurate measurement of strain within this range of frequencies (1–25 Hz) and amplitudes (100–3000 microstrain ($\mu\epsilon$)) is important for understanding the relationships between mechanical loading and bone remodeling.

A variety of methods exist for measuring animal bone strain in vitro and in vivo and are described, for example, in U.S. Pat. Nos. 5,456,724 and 5,695,496, both of which are herein incorporated by reference. Local strain in trabecular bone has been measured using optical devices to track the displacement of markers on individual trabeculae such as a method used by Michel M. C., et al in the technical article "Compressive Fatigue Behavior of Bovine Trabecular Bone," published in 1993—*J. Biomechanics* 26:453–463, and herein incorporated by reference.

Global strain has been measured in the tibia using metal-foil type strain gages adapted to intracortical pins that protrude from the skin as disclosed by Milgrom C., et al in "A Comparison of the Effect of Shoe Gear on Human Tibial Axial Strains Measured In Vivo" Abstract from ORS 43rd Annual Mtg., February 1997, and herein incorporated by reference.

The most common method has been to use metal foil type strain gages (for example, unstacked rosettes) bonded directly to the bone cortex. Surface-mounted gages are considered the standard for measuring cortical bone strain in vitro and in animal models in vivo. In humans, however, the use of surface-mounted gages is limited for several reasons; the compatibility of bonding material with living tissue is a problem (cyanoacrylate-based adhesives, which is the standard bonding material, are potentially carcinogenic), the level of invasiveness is high, and proper surface preparation, which is difficult to achieve on bone, is essential for obtaining reliable measurements. Among these methods, gages adapted to intracortical pins offer a less invasive and potentially more reliable way of obtaining in vivo strain data.

Surface-mounted strain gages when arranged in a rosette can provide principal strains and directions, and maximum shear strains within the plane of the gage. However, in the case of bone, where the moduli of cortical and trabecular bone vary greatly, surface strain gages mounted to the bone cortex are questionable indicators of global strain in trabecular bone. Further, if strains due to bending are to be calculated, surface gages must be mounted on opposing faces of the specimen, which is difficult to accomplish in vivo. Intracortical pins, which extend into the trabecular structure, can conceivably be used to follow global deformations and provide a measure of global strain across a section of bone in bending. Assumptions must be made that strain gradients are linear, and that the pins do not themselves deform. Also, as with unstacked strain gage rosettes, a uniform strain field is assumed in planes that contain the gage, as the gage necessarily covers a finite area of the test surface. Macroscopic (or average) strain is what is measured. For this reason, a smaller gage length is better. Since the porosity of the underlying cancellous bone restricts how small the gage length may be, a balance must be achieved between accurately capturing the strain field and sizing the gage length appropriately for a given specimen porosity. This is left to the user to determine for their particular. It is desired that means be provided for measuring in vivo strain encountered by the bones of a human and to do so with accuracy.

SUMMARY OF THE INVENTION

The present invention is directed to an extensometer, and a method of operation thereof, that measures intracortical pin displacement, from which strain is calculated, and from which, in a preferred embodiment, principal strain magnitudes and directions, maximum shear strain, and strains due to bending may be calculated via strain transformation relationships and geometric parameters of the extensometer.

The extensometer comprises at least two pins adapted to be inserted into the bone; and at least two capacitive sensors mounted across the pins and providing a variable capacitance whose output is varied by the strain to which the bone is subjected.

In a preferred embodiment, six sensors are arranged into three pairs with each pair being attached to a five (5) sided member and oriented from each other pair by an angle of 120 degrees.

BRIEF DESCRIPTION OF THE DRAWINGS

For a better understanding of the nature and objects of the present invention, reference should be made to the following detailed description taken in conjunction with the accompanying drawings, in which like parts are given like reference numbers, and wherein:

FIG. 1 is composed of FIGS. 1(A), 1(B) and 1(C), wherein FIG. 1(A) is a schematic elevational view showing the foot of a human, in particular, the calcaneus of a human serving as a site for in-vivo measurements by the present invention, and wherein

FIG. 7 is composed of FIGS. 7(A) and 7(B) that illustrate the geometric parameters associated with each intracortical pin lying at the apex of an equilateral triangle which is the basis for placement of the five-sided members making up the capacitive delta extensometer of the present invention.

FIG. 12 is composed of FIGS. 12((A), 12(B) and 12(C) that illustrate strain transformations related to the present invention.

FIG. 13 is composed of FIGS. 13(A) and 13(B) and illustrates a flow diagram of the present invention.

DETAILED DESCRIPTION OF THE PREFERRED EMBODIMENTS

Figure 1A:
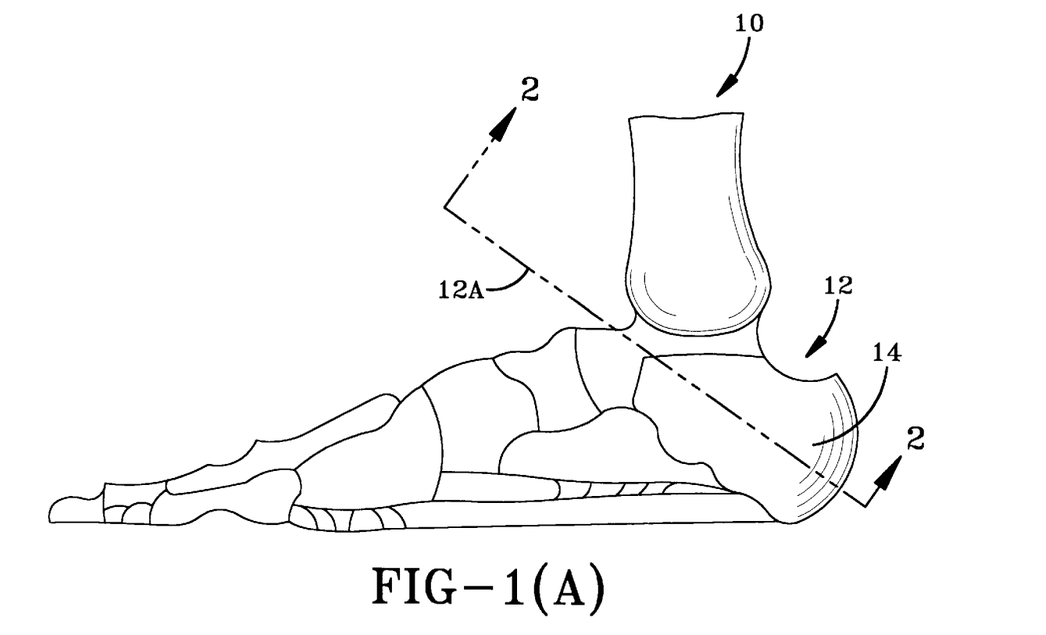
Figure 1B:
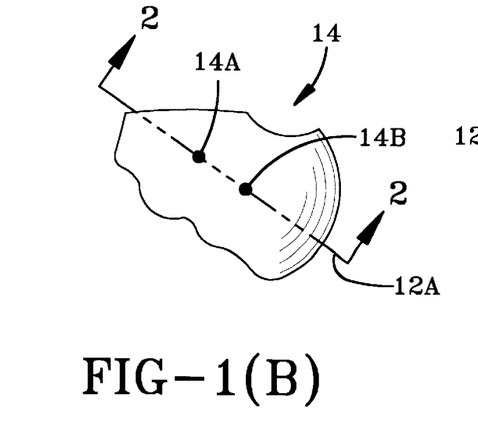
FIGS. 1(B) and 1(C) illustrates details of the sites.
Figure 1C:
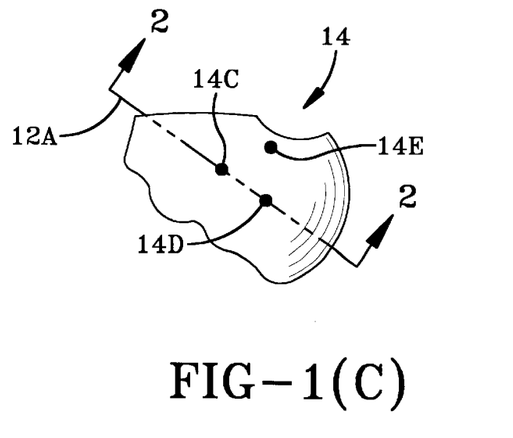

Referring now to the drawings, wherein the same reference number indicates the same element throughout, there is shown in FIG. 1 one application of the practice of the present invention. FIG. 1 is composed of FIGS. 1(A), 1(B) and 1(C), wherein FIG. 1(A) is a schematic view of the foot 10 of a human, in particular, the calcaneus 12 of a human serving as a site 14, running along line 12A, for in vivo measurement in accordance with the practice of the present invention.

FIG. 1(B) illustrates one measurement site defined by two points 14A and 14B running along the line 12A and associated with two intracortical pins to be described. FIG. 1(C) illustrates another measurement site defined by three points 14C, 14D and 14E, with point 14C intercepting the line 12A and points 14D and 14E straddling the line 12A and with the three defining points 14C, 14D and 14E being associated with three intracortical pins to be described. The measurement site of interest is left to the user's discretion; in this example the line 12A is roughly aligned along the principal orientation of trabeculae in the calcaneus. Although FIGS. 1(B) and 1(C) show typical locations, the intracortical pins may be inserted anywhere that measurement is to be taken in accordance with the present invention.

The measurements of the present invention detect the deformation of the bone, such as the calcaneus 12, and which deformation is converted into electronic signals which are routed to a processor, having routines running therein, for calculating strain in the bone. The strain is detected by extensometers, one arrangement of which may be further described with reference to FIG. 2 which is a view taken along line 2—2 of FIG. 1.

Figure 2:
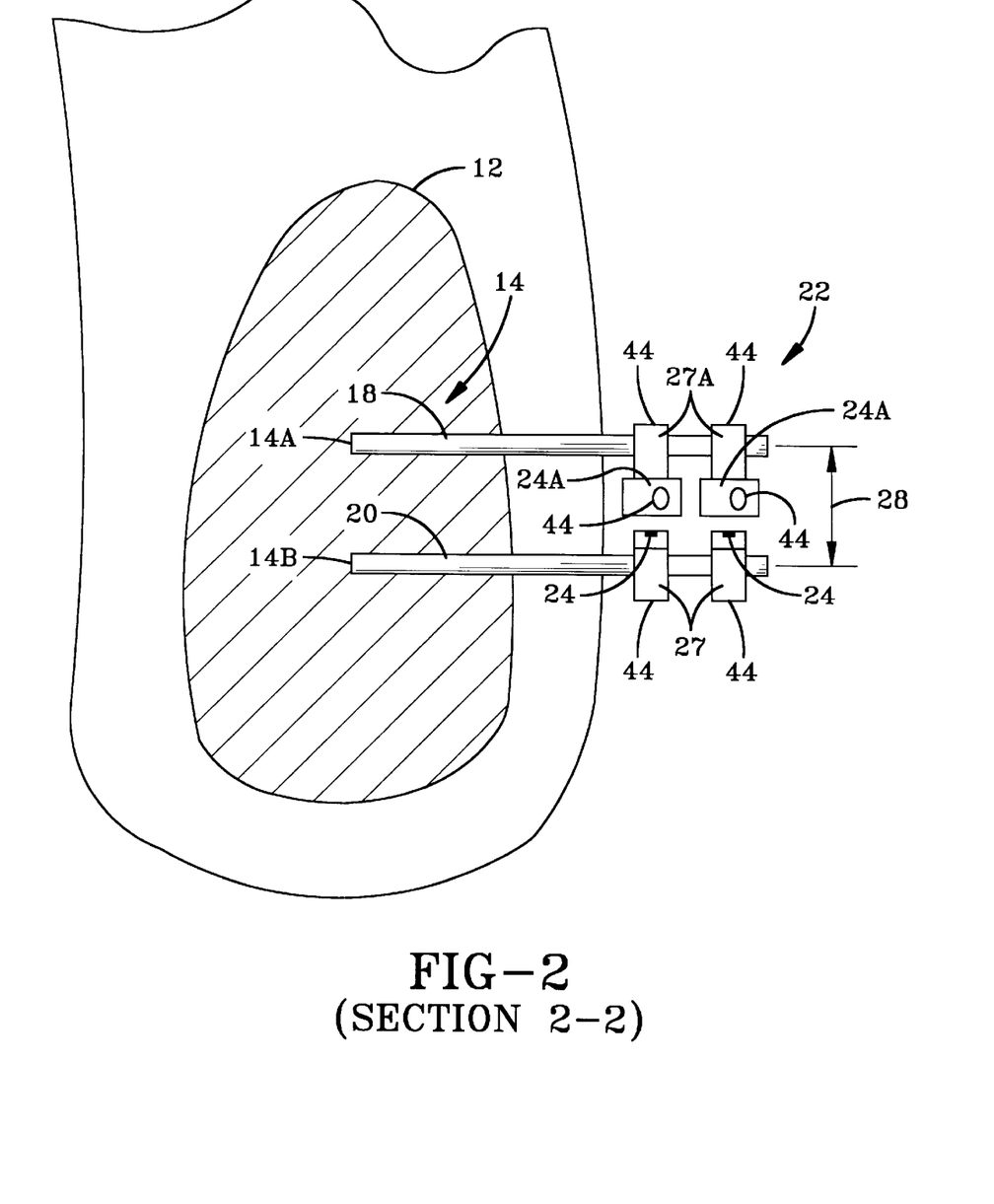
FIG. 2 illustrates the in vivo placement of a double sensor extensometer of the present invention.

FIG. 2 illustrates a double-sensor extensometer 22 that comprises at least two pins 18 and 20, respectively located at points 14A and 14B, already discussed with reference to FIG. 1(B), adapted to be inserted into the bone; and at least two capacitive sensors 24, made available by Capacitec, Inc., (Ayer, Mass.) with targets 24A mounted across the pins 18 and 20, respectively, and providing a variable capacitance whose output is varied by the strain experienced by bone 12. The targets 24A are conductive and grounded, and provide an adjustment capability so that the initial air gap may be changed. Targets 24A are held in place with set screws 44 (to be further described hereinafter). Sensors 24 are mounted to posts 27 which are insulated from the sensors. Targets 24A are mounted to posts 27A, which incorporate a machined end 29 (not shown) which is cylindrical in cross-section with a flat, against which the target set screw 44 rests. Posts 27 and 27A mount to pins 18 and 20. Posts 27 and 27A are held in place upon pins 18 and 20 by set screws 44 (not visible in view). The double-sensor extensometer 22 preferably has a guard ring 26 (not shown for the sake of clarity) made available from Capacitec Inc., and having a 0.156" inch outer ring preferably surrounding the sensors 24 and minimizing distortion, or fringing effects on the electrostatic field created by the capacitor. The outer edges of intracortical pins 18 and 20 are spaced apart from each other by a gauge length 28. The gage length 28 is allowed to change, depending on the user's needs. For example, if the user expects high strain values within site 14, a larger gage length may be desired. On the other hand, if the user is interested in capturing more accurate strains, or the strain field beneath the gage is expected to have high strain gradients, the gage length 28 might need to be smaller. A gage length 28 of 0.524 inches may be a typical value to serve as a place to start these trade-off considerations by the user.

The sensors 24 may each be a non-contact displacement transducer made available from Capacitec, Inc., as their type HPB-75/156B-A-13-B-15-B-D probe. The intracortical pins 18 and 20 may each be comprised of stainless steel K-wire and have a diameter of 0.078 inches.

The double-sensor extensometer 22 has the at least two sensors 24 spaced some distance apart so as to define the angle between pins 18 and 20. Using geometric variables measured from the double-sensor extensometer 22 and displacement data from each of the two sensors 24, it is possible to calculate a corrected strain within the region of bone 12, in a manner as to be described hereinafter with reference to FIG. 14. A further embodiment of the present invention may be further described with reference to FIG. 3.

Figure 3:
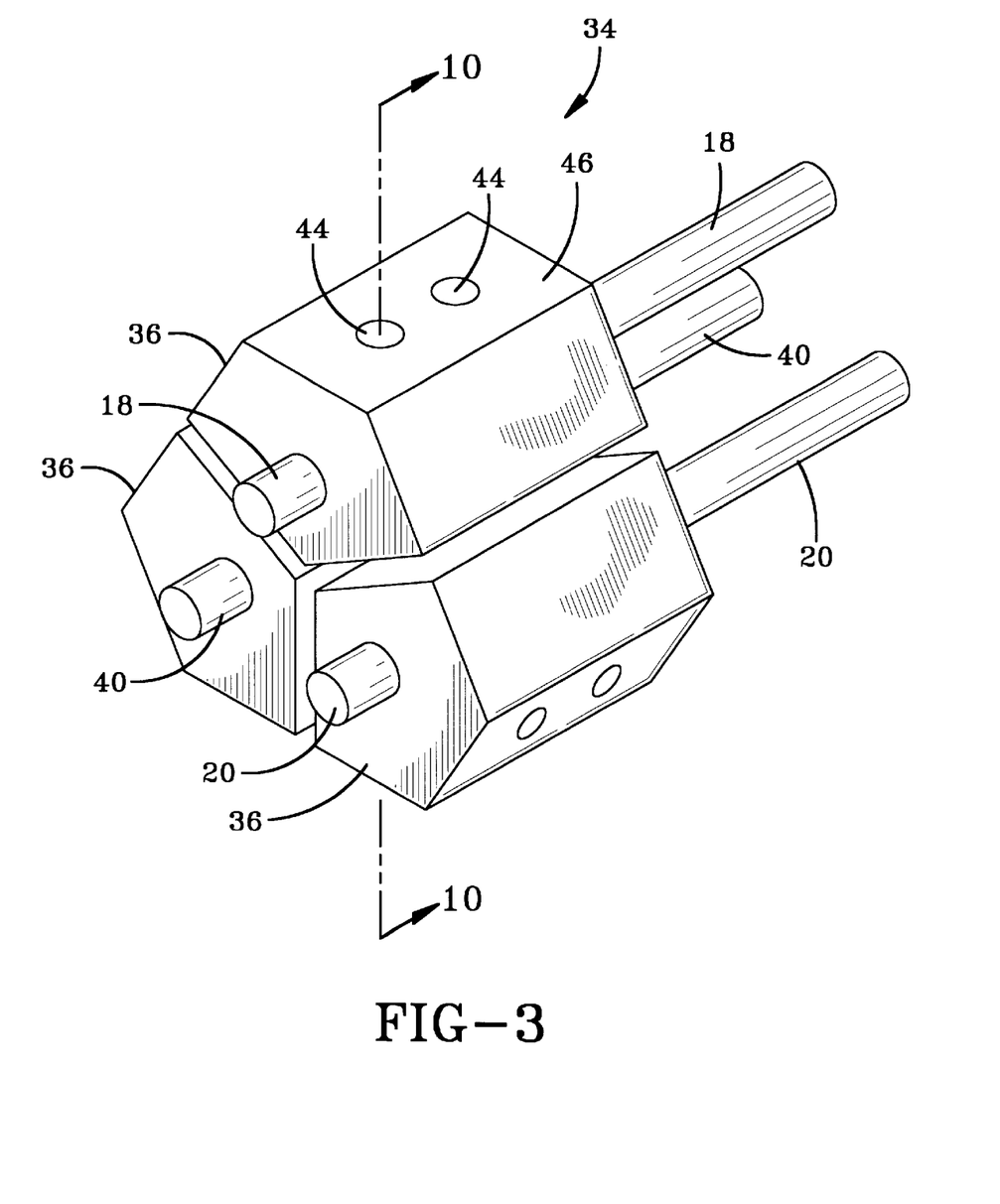
FIG. 3 illustrates the capacitive delta extensometer of the present invention.

FIG. 3 illustrates a herein termed "capacitive delta extensometer" 34, which has the benefits of an extensometer, known in the art, which is used to measure axial strain, as well as the additional benefits of providing principal strain magnitudes and direction, maximum shear strain, and strain due to bending. Further details of extensometers may be found in U.S. Pat. Nos. 4,160,325; 4,251,918; 4,607,531; and 4,939,445, all of which are herein incorporated by reference.

The capacitive delta extensometer 34 comprises three (3) identical five-sided members 36 each of which carry a pair of capacitive sensors 38 (not shown in FIG. 3) spaced apart from each other and oriented with respect to each pair by a value of 120 degrees, as will be further described hereinafter with reference to FIG. 10. The capacitive delta extensometer 34 carries three intracortical pins 18, 20 and 40.

Figure 4:
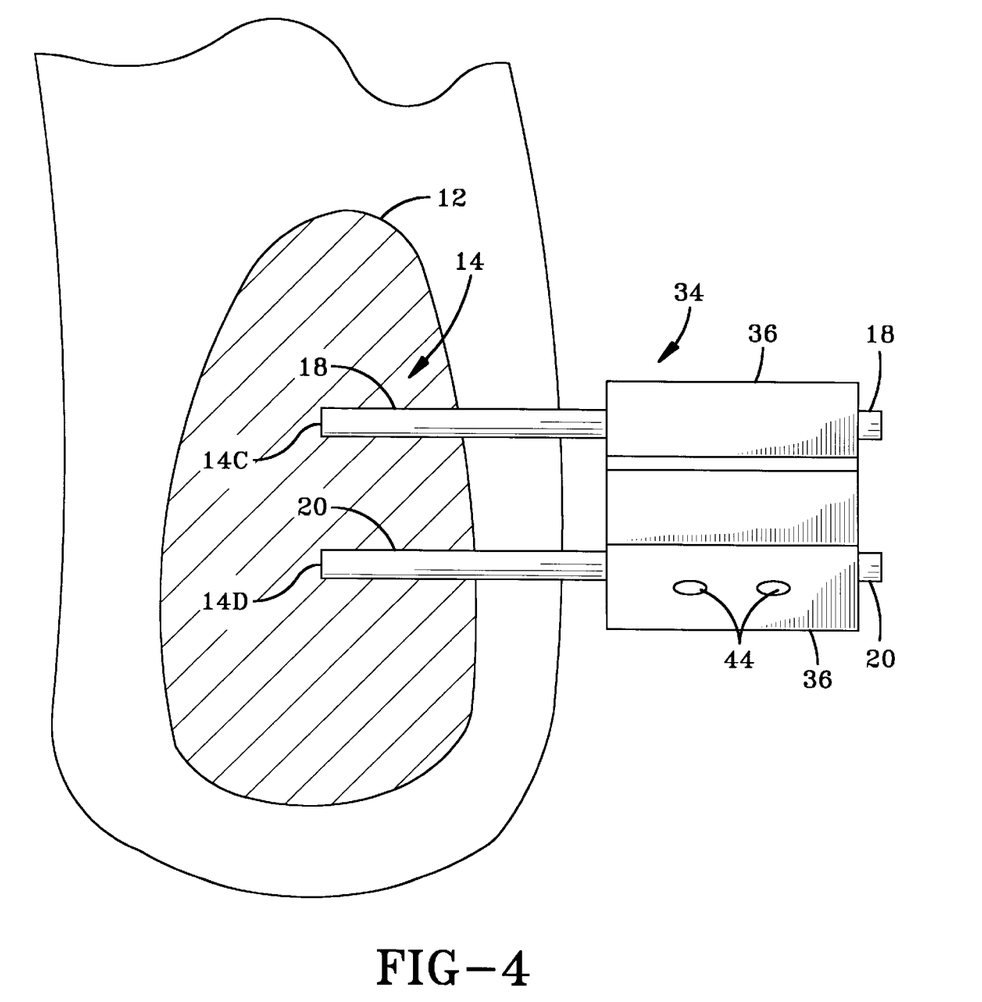
FIG. 4 illustrates the in vivo placement of the capacitive delta extensometer of the present invention.

The capacitive delta extensometer 34 is shown in FIG. 4 in a pictorial view as being embedded in the calcaneus bone 12 shown in cross-section of the foot 10. The intracortical pin 40 of FIG. 3 is out of view for the cross-section of FIG. 4, but all three pins 18, 20 and 40 are present and their placement is that of FIG. 1(C) having defining points 14C, 14D and 14E. The capacitive delta extensometer 34 may be further described with reference to FIG. 5.

Figure 5:
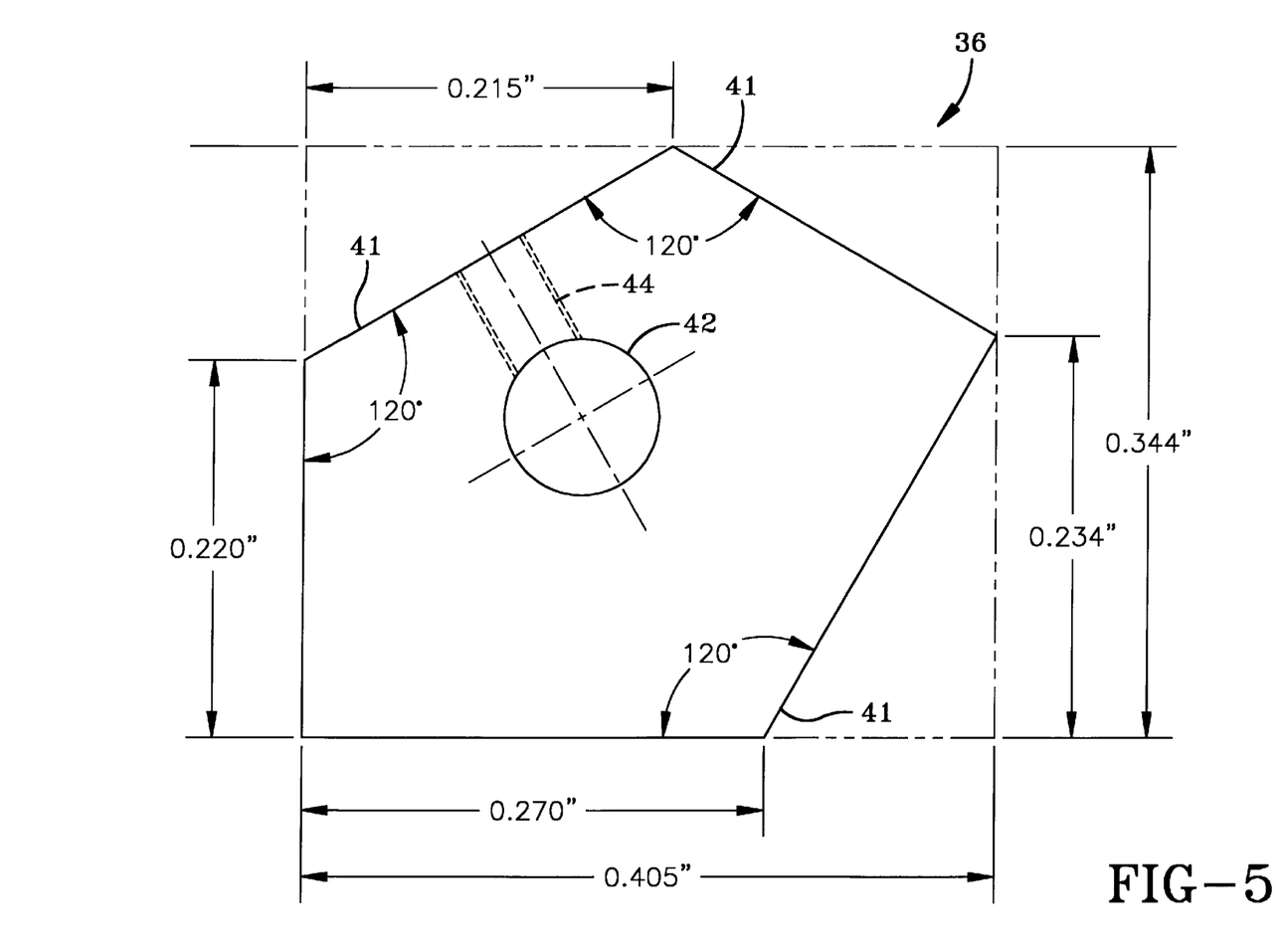
FIGS. 5 and 6 illustrate further details of the capacitive delta extensometer of FIG. 3.

FIG. 5 illustrates typical dimensions of the five-sided member 36, three of which members make up the capacitive delta extensometer 34 of the present invention. Although FIG. 5 illustrates the typical dimensions in great detail, the dimensions shown in FIG. 5 should not be considered as limiting features of the invention in any manner whatsoever.

The five-sided member 36 allows for the ability to orient the sensors 38 of the capacitive delta extensometer 34 by a preferred 120 degrees. More particularly, the five-sided member 36 has three corners identified with the reference number 41 and showing the angle of 120 degrees. These three corners may be used to obtain the desired orientation of 120 degrees between each pair of the sensors 38 to be described hereinafter with reference to FIG. 10. The five-sided member 36 has first and second apertures 42 and 44 respectively serving as the aperture through which either of the intracortical pins 18, 20 or 40 extends and the aperture through which set screw 44, is inserted so as to affix each of the five-sided members 36 to its related intracortical pin 18, 20 or 40. The five-sided member 36 may be further described with reference to FIG. 6 which is composed of FIGS. 6(A), 6(B), and 6(C).

Figure 6A:
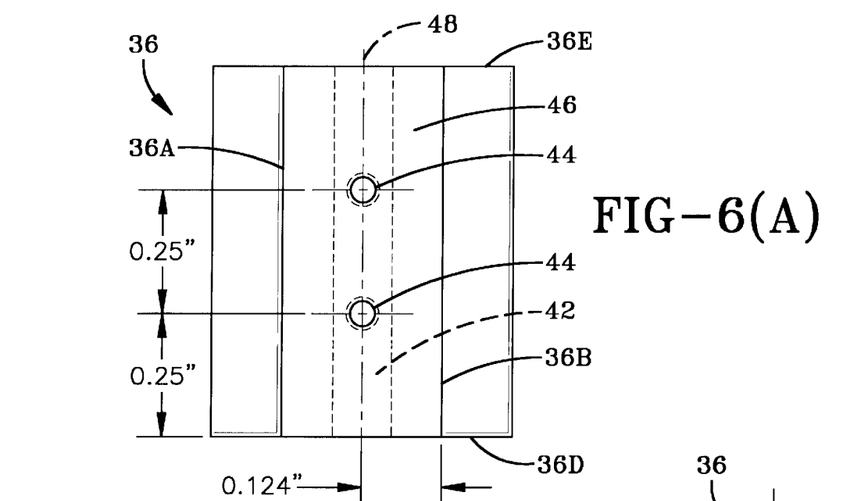
Figure 6B:
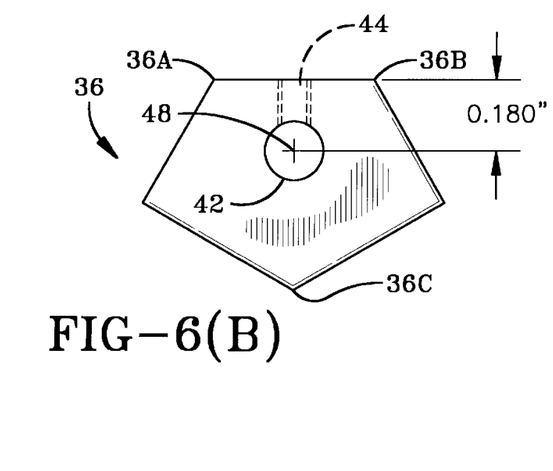
Figure 6C:
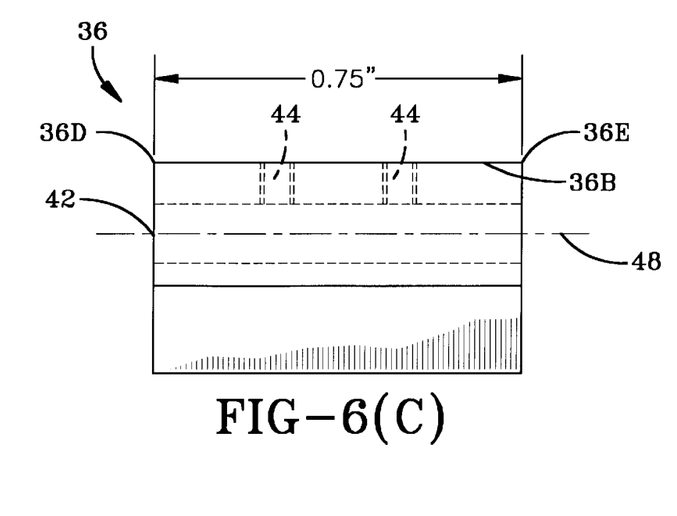

FIG. 6(A) shows a side 46, also shown in FIG. 3 along with apertures 44, of the five-sided member 36 which is herein termed "the set screw side." More particularly, side 46 is the side of the five-sided member 36 in which set screws (not shown) are inserted and screwed into aperture 44 having screw threads and a centerpoint which corresponds to the axis 48 of the five-sided member 36. The reference number 44 may be used in an interchangeable manner to identify "apertures 44" and "set screws 44." FIG. 6(A) further illustrates that each of the apertures 44 for the set screws are spaced apart from each other by a predetermined distance, such as 0.25 inches and with one of the apertures 44 spaced from a front edge of the five-sided member 36 by the same 0.25 distance. The axis 48 is also the axis for the aperture 42 and the axis 48 and is located at a predetermined distance such as 0.180 from top edges 36A and 36B which are also shown in FIG. 6(B). The distance the pins 18, 20 and 40 are spaced apart from each other is similar to the gage length 28 of FIG. 2. FIG. 6(A) also shows outer edges 36D and 36E of the five-sided member 36 and which outer edges are shown in FIG. 6(C) having a typical separation of 0.75 inches.

The five-sided member 36 of FIGS. 5 and 6 provides for the proper alignment of the sensors 38 and also provides for the proper air gaps within a linear range of the sensors 38 so as to provide for proper operation of the capacitive delta extensometer 34. The capacitive delta extensometer 34 is mated to the three intracortical pins 18, 20 and 40 by way of aperture 42 with each pin positioned at the apex of an equilateral triangle provided by the three five-sided members 36 which may be further described with reference to FIG. 7 composed of FIGS. 7(A) and 7(B).

Figure 7A:
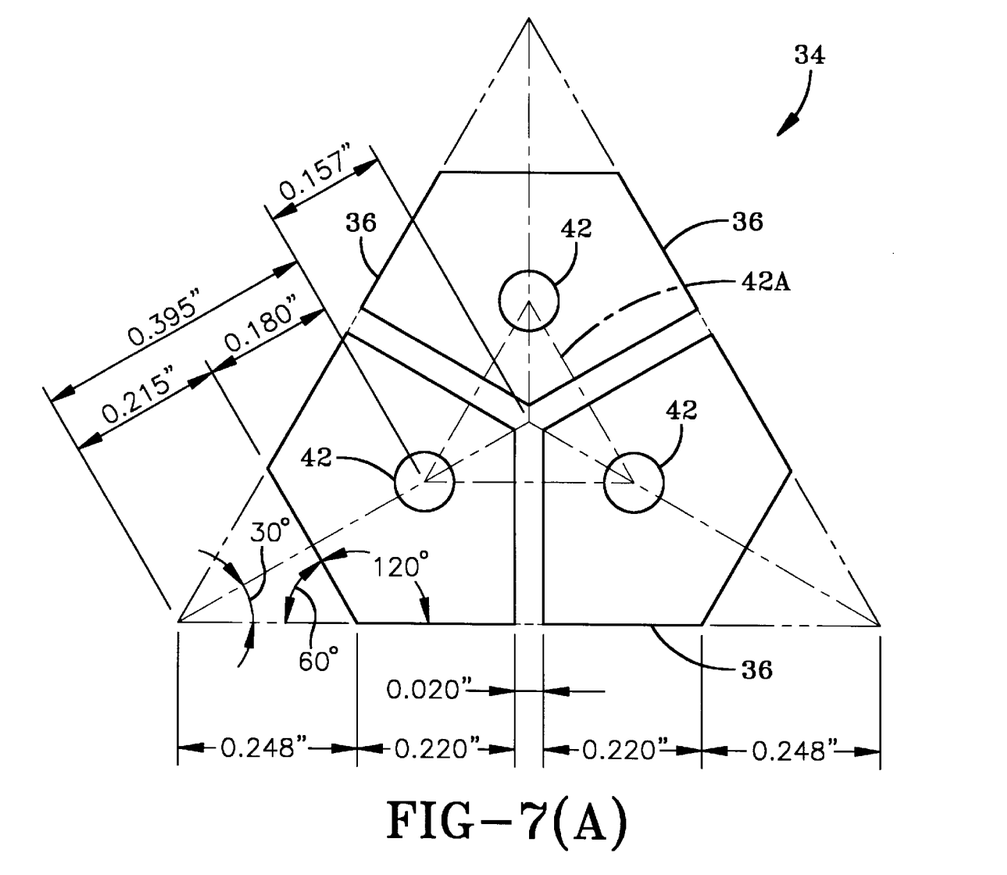

FIG. 7(A) illustrates three five-sided members separated from each other by a typical distance of 0.020 inches and arranged to form the capacitive delta extensometer 34 and also having typical dimensions shown therein, as well as interconnecting dimensional lines so as to indicate appropriate angles thereof. FIG. 7(A) shows an equilateral triangle 42A interconnecting the apertures 42. From the dimensions shown in FIG. 7(A), it may be determined that the sides of equilateral triangle 42A may each have a typical value of 0.272 inches as shown in FIG. 7(B).

Figure 7B:
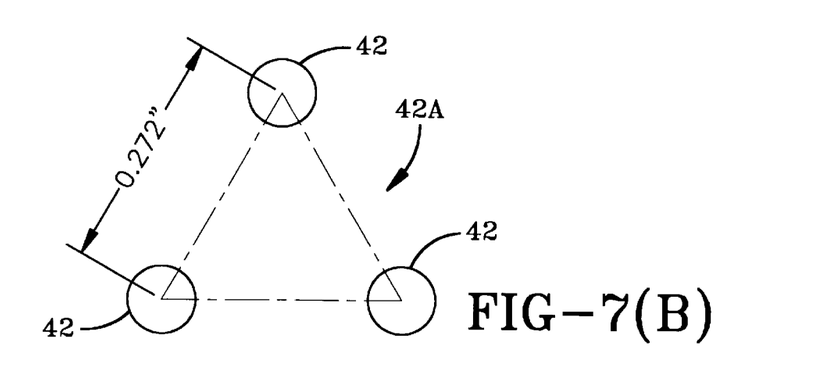

From the parameters shown in FIGS. 7(A) and 7(B) and using a typical diameter of 0.078 inches for each of the intracortical pins 18, 20 and 40, it may be determined the gage length, that is the separation between pins 18, 20 and 40 is 0.350 inches (0.272+0.078).

In the assembly procedure for the capacitive delta extensometer 34, it is desired that a drilling guide be provided and used to ensure accurate placement of pins 18, 20 or 40 into specimen, such as site 14, and so that the pins 18, 20 and 40 are parallel to one another. Once the pins 18, 20 and 40 are in place, the five (5)-sided members 36 may be mounted to the pins 18, 20 and 40 and properly aligned. The arrangement shown in FIG. 7 may be used as a template for making a drill and placement guide for the capacitive delta extensometer 34. The capacitive delta extensometer 34 having the typical dimensions of FIGS. 5, 6 and 7 may be further described with reference to FIG. 8.

Figure 8:
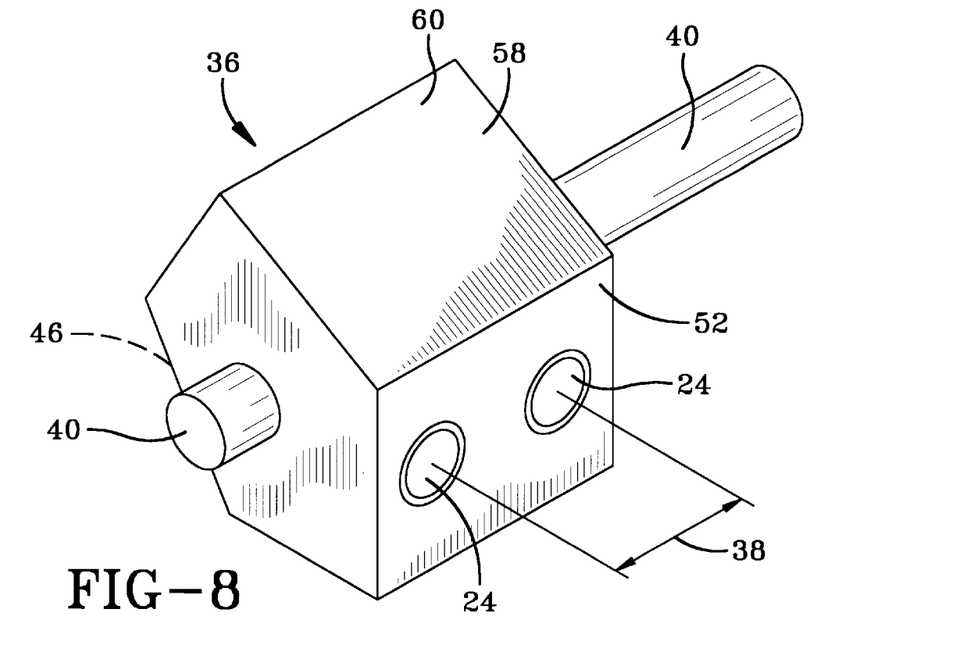
FIG. 8 illustrates further details of the capacitive delta extensometer of FIG. 4.

FIG. 8 illustrates one of three five-sided members 36 of capacitive delta extensometer 34 as having a face 52, that is its sensor face, positioned in the direction of the opposing target face, such as 58. The direction in which the five-sided member 36 is placed into the specimen 14 is not critical so long as the pins 18, 20 and 40 are long enough to extend into specimen 14. The five-sided member 36 further has a target face 58, as well as the set-screw side 46 of FIG. 6(A). The sensor face 52 has attached thereto two sensors 24, that is, a sensor pair, placed at a predetermined distance 38 apart from each other, and having a typical value of 0.50 inches. The sensor face 52 is positioned in the direction of the next five-sided member's 36 target face 58. The sensors 24 used in this embodiment of the capacitive delta extensometer 34 are disk-shaped "button probes," with a sensor O.D. of 0.075" and a linear range of 0.050", typical. The target face 58 has mounted to it a thin, conductive material 60 such as aluminized mylar (or aluminum tape) which is grounded. The conductive material 60 acts as one-half of the capacitor for each of sensor 24 opposing it in a manner similar to 24A in FIG. 2.

The function of each sensor pair comprised of the two sensors 24 is to define two points on the intracortical pin, such as pins 18, 20 and 40, such that the position of either pin 18, 20 or 40 in two-dimensional (2D) space at any point along its length may be calculated. The displacement of pin 20 relative to pin 40, for example, is defined in the plane containing pins 20 and 40, and the displacement of pins 20 and 18, for example, is defined in the plane containing pins 20 and 18. In this way, the pin displacement measurement is analogous to measuring % elongation of a single uniaxial gage element contained in a strain gage rosette arrangement known in the art. For such calculations, it is assumed that none of the pins 18, 20 and 40 deforms rather, their movement is defined as a translation plus a rotation within planes as described above. A further embodiment of the capacitive delta extensometer 34 may be further described with reference to FIG. 9.

Figure 9:
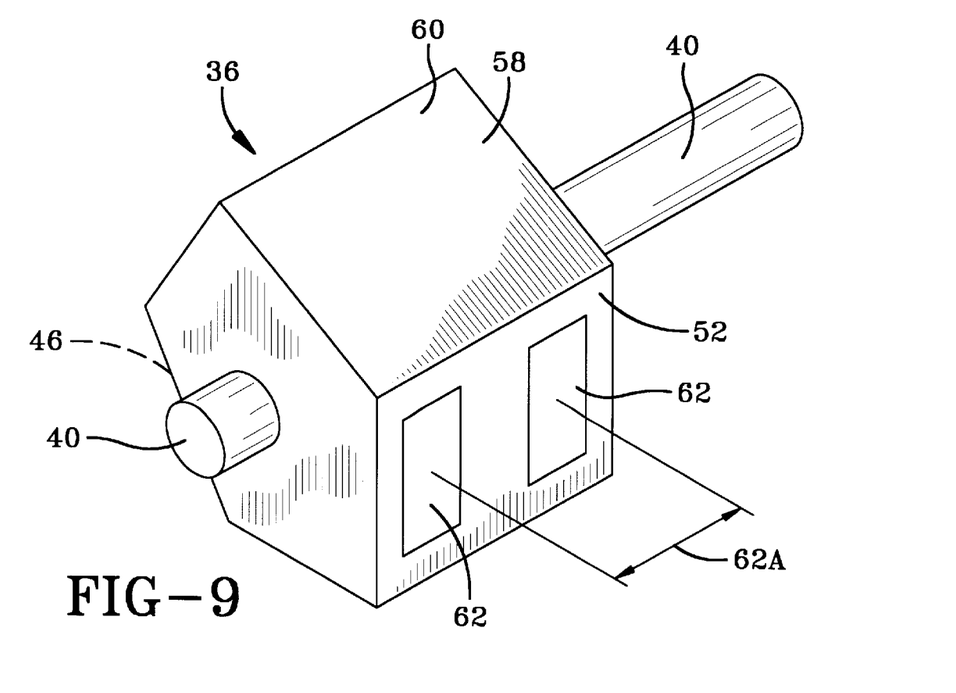
FIG. 9 illustrates another embodiment of a capacitive delta extensometer.

FIG. 9 is similar to FIG. 8 with the exception that the capacitive sensors 24 of FIG. 8 have been replaced by rectangular shaped thin sensors 62 separated from each other by a distance 62A having values similar to those of 38 of FIG. 8. The rectangular faces measure 0.039 by 0.157 inches, typical, and have a thickness=0.0063 inches nominal. Both of the capacitive delta extensometer 34 embodiments of sensor 24 or 62 of FIGS. 8 and 9 may be further described with reference to FIG. 10, which is a view taken along line 10—10 of FIG. 3.

Figure 10:
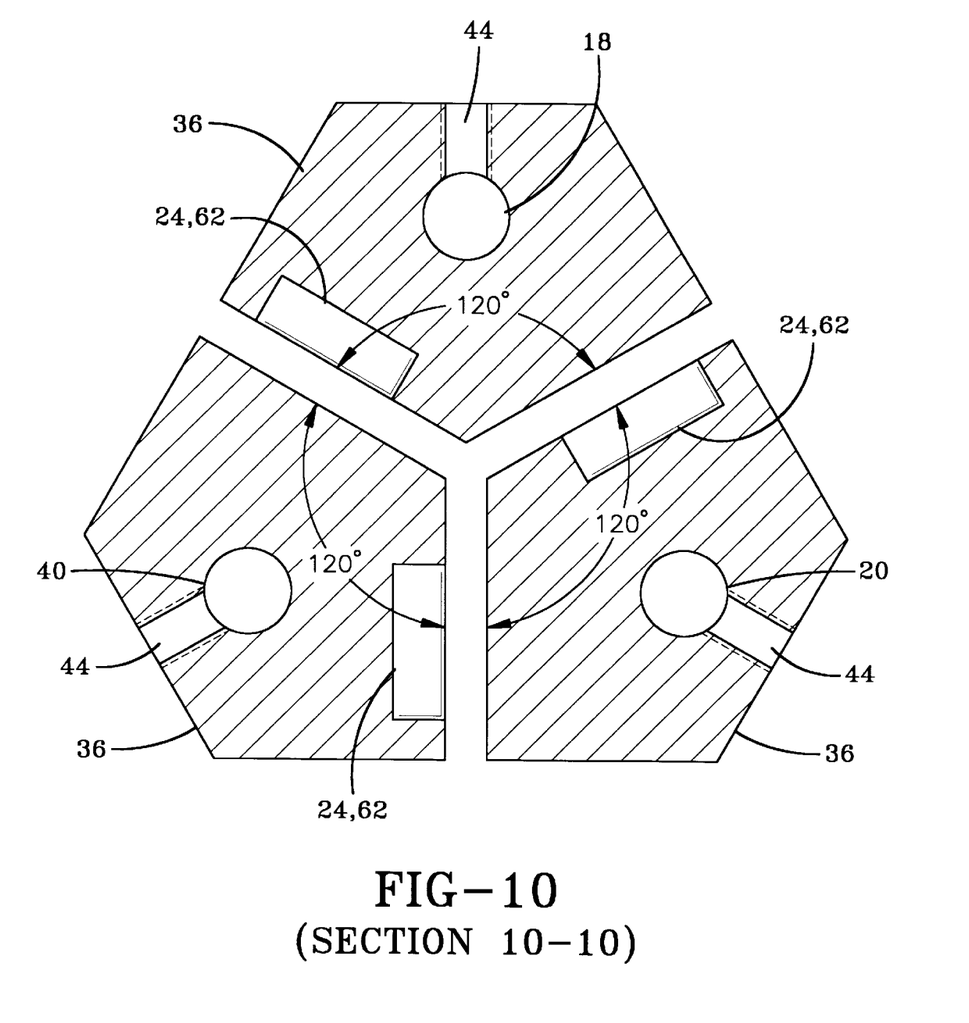
FIG. 10 is a cross-sectional view of the capacitive delta extensometer taken along line 10—10 of FIG. 3, and illustrates the orientation of pairs of the sensors thereof displaced from each other by 120 degrees.

FIG. 10 illustrates the sensors 24 or 62 oriented 120 degrees with respect to each other. It should be recognized that each of the sensors 24 or 62 on each of the three five-sided members 36 cooperates with its other sensors 24 or 62 (not shown in FIG. 10 but shown in FIGS. 8 and 9) making up its pair and each pair of sensors of each of the five-sided member 36 is oriented by the desired 120 degrees. The sensor, such as sensor 24, is mounted to an insulated base to the intracortical pin 18, 20 or 40, which may be accomplished by making the five-sided member 36 out of a non-conductive material, whereas the other half of the capacitor, that is, surface 60, is conductive and grounded. Sensors are typically mounted in place using cyanoacrylate-based adhesive.

Operation of the Present Invention

Figure 11:
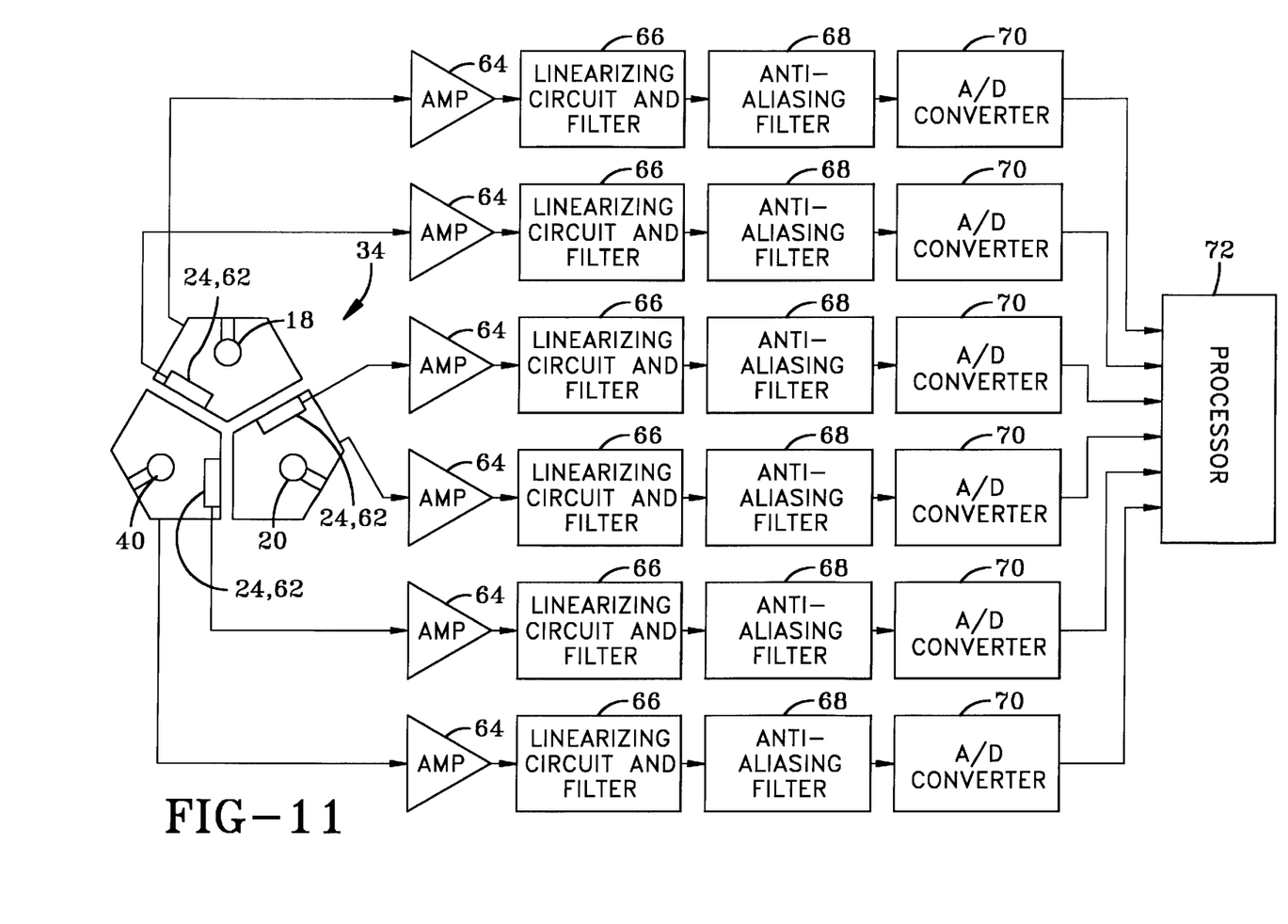
FIG. 11 is a block diagram of the electronic equipment for processing the output signals generated by the capacitive delta extensometer of the present invention.

The operation of the present invention may be described with reference to FIG. 11 which is a block diagram of the electronics used to process the displacement output of the sensors 24 or 62 arranged 120 degrees apart from each other, as discussed with reference to FIG. 10 and as generally illustrated in FIG. 11 for the capacitive delta extensometer 34. Each of the six (6) sensors provides an electrical output signal corresponding to the displacement that it senses and each of which electrical signal is routed to a serial arrangement comprising an amplifier 64, preferably a linearizing circuit and low pass filter 66, preferably an anti-aliasing filter 68, and an analog-to-digital converter 70. Each of the serial arrangements for each of the six (6) sensors is routed to a processor 72.

Each of the sensor amplifiers 64 uses a linear capacitive reactance technique for converting the displacement of the variable capacitor of each of the capacitive sensors 24 or 62 to a voltage output which results in increased sensitivity with decreasing sensor area. Each of the sensors 24 or 62 detects a strain that is resolved to +/−four (4) to +/−eight 8 $\mu\epsilon$ for a 0.524 inch gage length device or +/−15 $\mu\epsilon$ for a 0.272 inch gage length device. This +/−4 $\mu\epsilon$ is obtained by using sensors that are calibrated within the range of 0.040 inches, for example, and an amplifier having output in the range of 0–10V with +/−0.001 volt resolution.

The separation, such as 38 of FIG. 8, of the sensors 24 may be selected to be 0.500, inches but can be changed by mounting the sensors closer or further apart. The capacitive delta extensometer 34 maintains an air gap (separation between the five-sided members 36), shown in FIG. 7, throughout the strain measurements and this air gap may be set to about 0.020 inches. The amplifier 64 preferably contains the linearizing circuit and low pass filter.

The A/D converter 70 may be made available from National Instruments as their AT-M10-16E-10 type. Each of the A/D converters 70 provides a digital representation that is routed to a processor 72 which may be a PC.

Operating routines within the processor 72 accept the measurements from each of the sensor paths and calculate the strain reading due to specimen deformation. Basically the routines provide a line which is defined by a space between two (2) points, with each line corresponding to each intracortical pin. The two (2) points defining the position are determined by the sensors mounted at their known points along the length. The data reduction program incorporates calculations of the effective strain in the region of the bone based on strain time-history paths and sensor geometry variables. Strain-transformation relationships are used to calculate the principal strain directions and magnitudes and maximum shear strains in the specimen. The strain transformations related to the present invention may be further described with reference to FIG. 12 composed of FIGS. 12(A), 12(B) and 12(C).

Figure 12A:
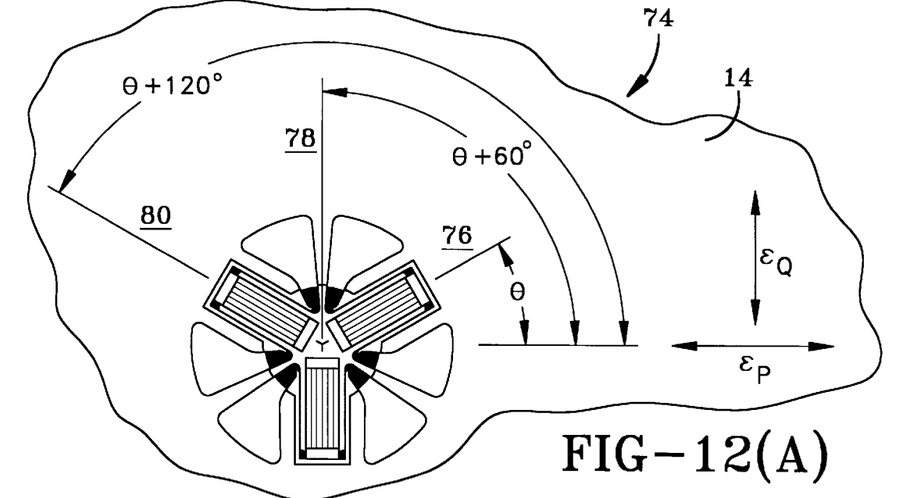

FIG. 12(A) illustrates a delta rosette orientation, known in the art, for a sensor installed on a test surface, such as site 14, with a first grid 76 at an angle $\Theta$ from the major principal strain direction, $\epsilon_P$. FIG. 12(A) further illustrates a strain direction, $\epsilon_Q$ which is perpendicular to $\epsilon_P$ and also illustrates second and third grids 78 and 80 respectively.

Figure 12B:
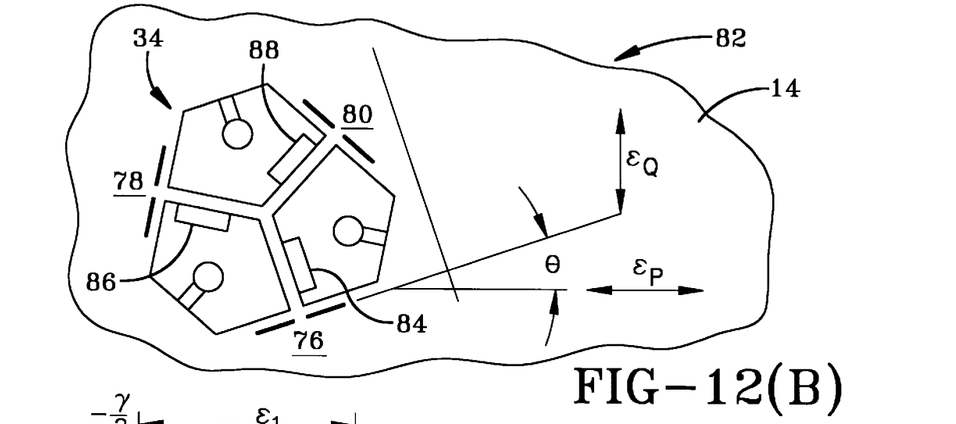

FIG. 12(B) illustrates the rosette grid axes of FIG. 12(A) resulting in an orientation 82 related to the capacitive delta extensometer 34 of FIG. 10. The orientation 82 is analogous to the sensor of the capacitive delta extensometer 34 of FIG. 3. From FIG. 12(B) it should be noted that, for example, the second grid 78 is to be viewed as +60° (CCW) from grid 76 in the rosette of FIG. 12(A), and +120° in Mohr's circle of FIG. 12(B). FIG. 12(B) further illustrates the capacitive delta extensometer 34 as carrying sensors indicated by reference numbers 84, 86 and 88, wherein 84 represents a sensor-pair aligned with the first grid 76 of FIG. 12(A), 86 represents a sensor-pair aligned with the second grid 78 of FIG. 12(A), and 88 represents a sensor-pair aligned with the third grid 80 of FIG. 12(A).

Figure 12C:
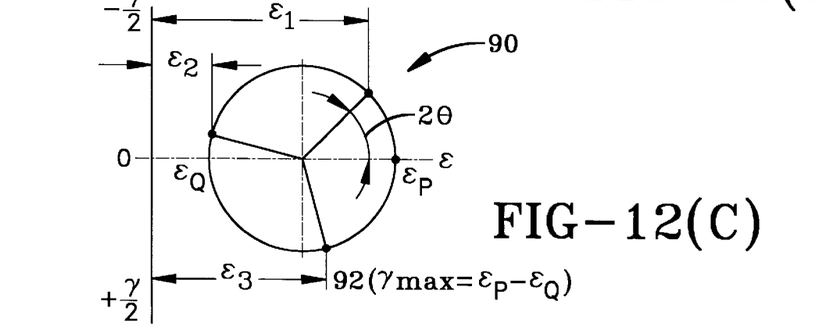

FIG. 12(C) illustrates the parameters of the Mohr's circle, generally identified by reference number 90, for strain and including strains $\epsilon_1$, $\epsilon_2$ and $\epsilon_3$, as well as maximum shear strain 92 shown as $\gamma$ max=$\epsilon_P$-$\epsilon_Q$ determined by operating routines being run in the processor 72. It is important to note that the plane containing strains as represented by Mohr's circle for strain in FIG. 12(C) is chosen by the user, and is a plane different than those planes containing sensors. The strains represented in FIG. 12(C) are developed through a procedure described below. The overall operation 94 of the routines running in the processor 72 are shown in FIG. 13 which is comprised of FIGS. 13(A) and 13(B).

Figure 13A:
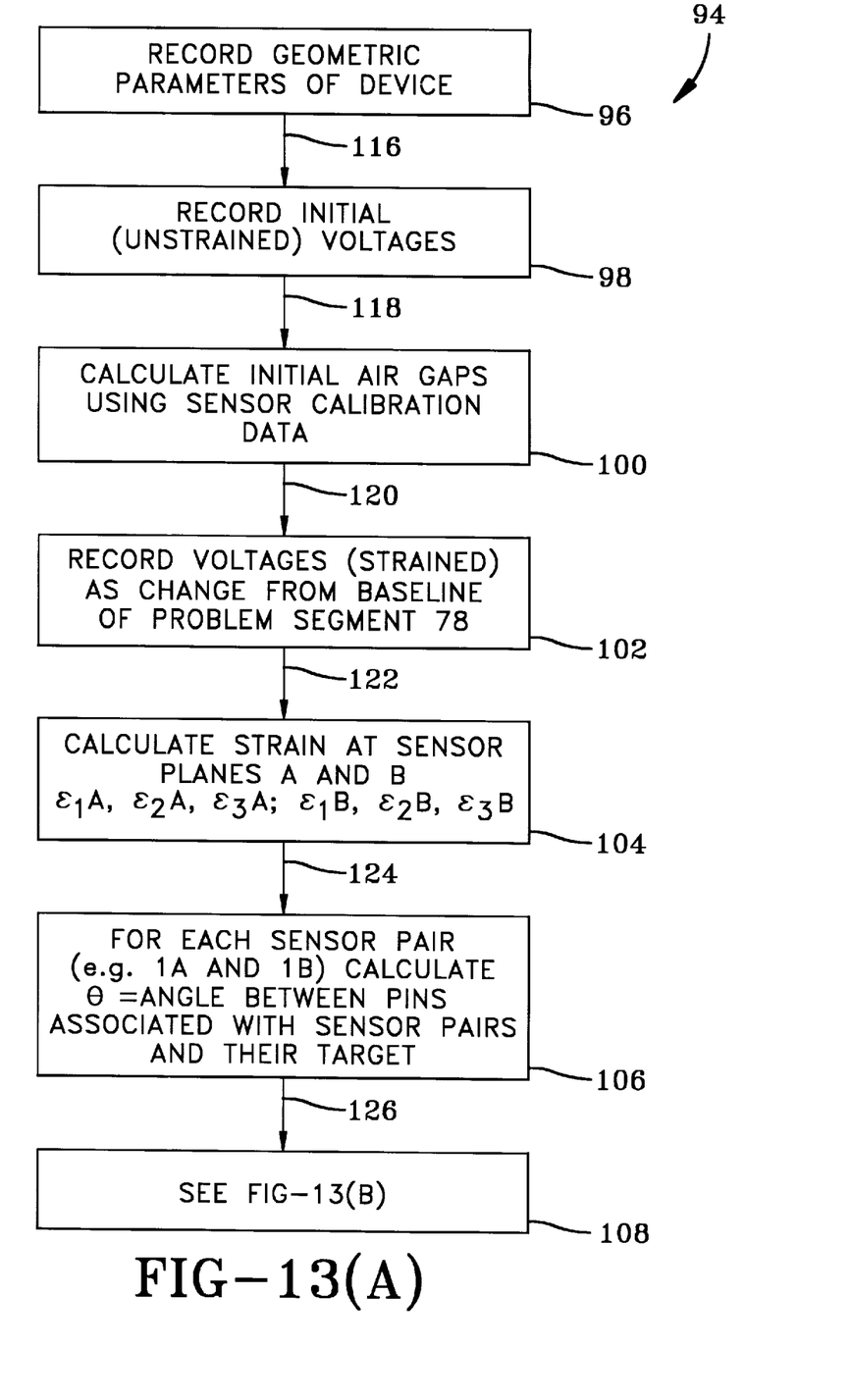
Figure 13B:
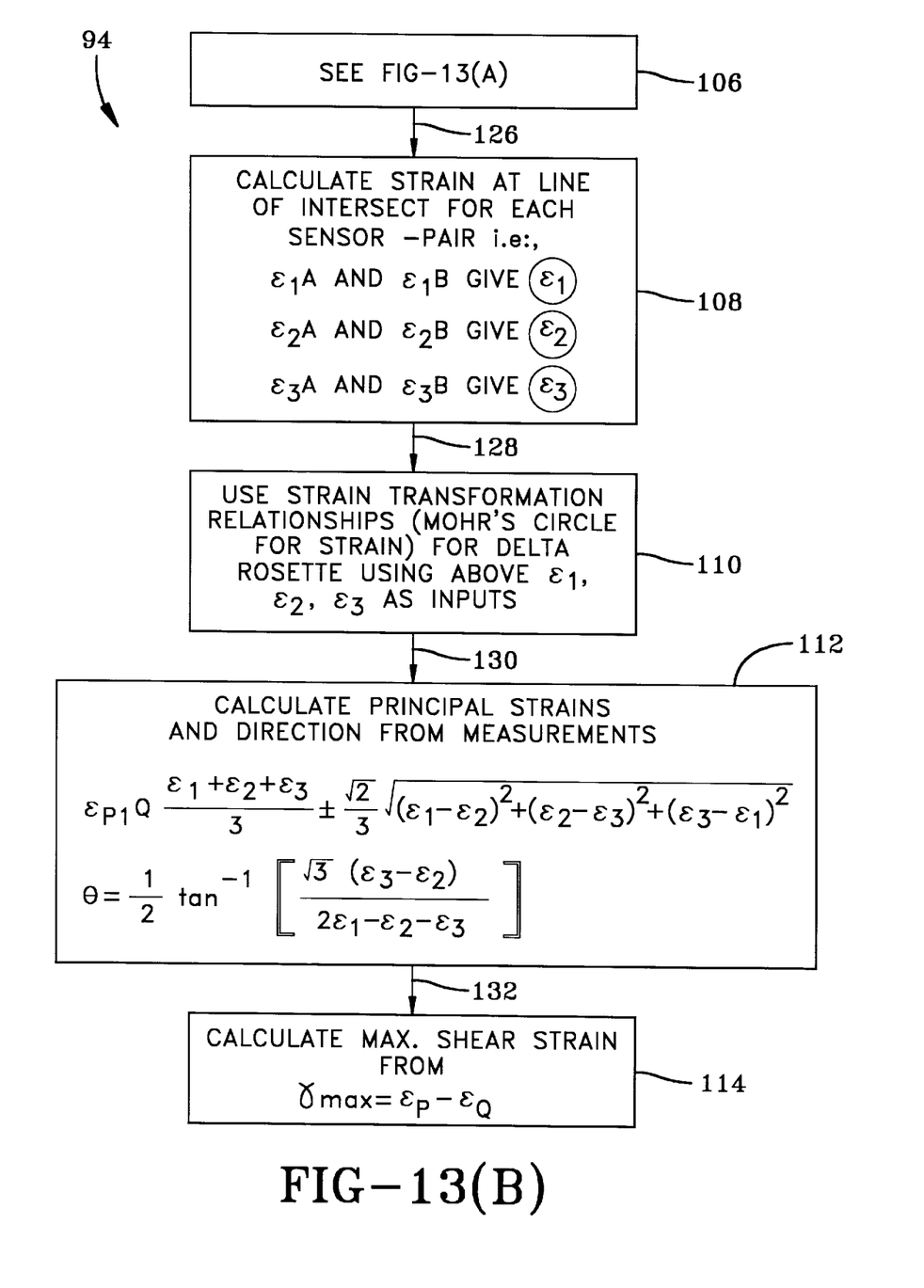

The overall operation 94 is comprised of program segments 96–114, wherein program segment 96 of FIG. 13(A) records (from manual inputs) geometric parameters of FIGS. 5–9 of the device being used, such as the capacitive delta extensometer 34, and then passes control to program segment 98 by way of signal path 116.

Program segment 98 records the initial (unstrained) voltage of all six sensors, such as those of FIG. 11 and then passes control to program segment 100 by way of signal path 128.

Program segment 100 calculates the initial air gaps using sensor calibration data supplied by manufacturer or determined by user and then passes control to program segment 102 by way of signal path 120.

Program segment 102 records voltages (strained) as a change from baseline, that is, from the initially recorded voltages of program segment 98, and then passes control to program segment 104 by way of signal path 122.

Program segment 104 calculates strain at the planes for the three pairs of sensors. For example, with reference to FIG. 12(B), it is seen that one plane, defined as A, would be common to all three sensors 84, 86 and 88 and that another plane, defined as B, would be common to the other three sensors (not shown in FIG. 12(B) associated with the three sensors 84, 86 and 88. The strain, $\epsilon$, at the planes A and B may be defined as $\epsilon_1 A, \epsilon_2 A, \epsilon_3 A$; $\epsilon_1 B, \epsilon_2 B, \epsilon_3 B$. After segment 104 performs its calculations, program segment 104 passes control to program segment 106 by way of signal path 124.

Program segment 106 for each sensor pair calculates $\Theta$=angle, shown in FIG. 12(A), between pins 18, 20 or 40, associated with a particular sensor pair, and their target face by using sensed displacements and geometric parameters obtained in program segment 96. After these calculations, program segment 106 passes control to program segment 108 of FIG. 13(B) by way of signal path 126.

Program segment 108 calculates strain at the line of interest, for each sensor pair 84, 86 or 88. These calculations yield the following results: i.e., $\epsilon_1 A$ and $\epsilon_1 B$ yields $\epsilon_1$, $\epsilon_2 A$ and $\epsilon_2 B$ yields $\epsilon_2$, and $\epsilon_3 A$ and $\epsilon_3 B$ yields $\epsilon_3$, wherein $\epsilon_1$, $\epsilon_2$ and $\epsilon_3$ are shown in FIG. 12(C). After such calculations, program segment 108 passes control to program segment 110 by way of signal path 128.

Program segment 110 uses strain transformation relationships, such as Mohr's circle for strain, known in the art and shown in FIG. 12(C), for a delta rosette, also known in the art, using program segment 108 quantities $\epsilon_1, \epsilon_2, \epsilon_3$ as inputs. After such calculations, program segment 110 passes control to program segment 112 by way of signal path 130.

Program segment 112 calculates principal strains $\epsilon_{P,Q}$ and direction $\Theta$ from measurements given below by expressions (1) and (2), known in the art:

$$\epsilon_{P,Q} = \frac{\epsilon_1 + \epsilon_2 + \epsilon_3}{3} \pm \frac{\sqrt{2}}{3} \sqrt{(\epsilon_1 - \epsilon_2)^2 + (\epsilon_2 - \epsilon_3)^2 + (\epsilon_3 - \epsilon_1)^2} \qquad 1$$

$$\Theta = \frac{1}{2}^{-1} \left[ \frac{\sqrt{3}(\epsilon_3 - \epsilon_2)}{2\epsilon_1 - \epsilon_2 - \epsilon_3} \right] \qquad 2$$

After program segment 112 completes its calculations it passes control to program segment 114 by way of signal path 132.

Program segment 114 calculates maximum shear strain from; $\gamma_{max} = \epsilon_P - \epsilon_Q$. The completion of the calculations of program segment 114 corresponds to the completion of the routines 94.

Practice of the Invention

Figure 14:
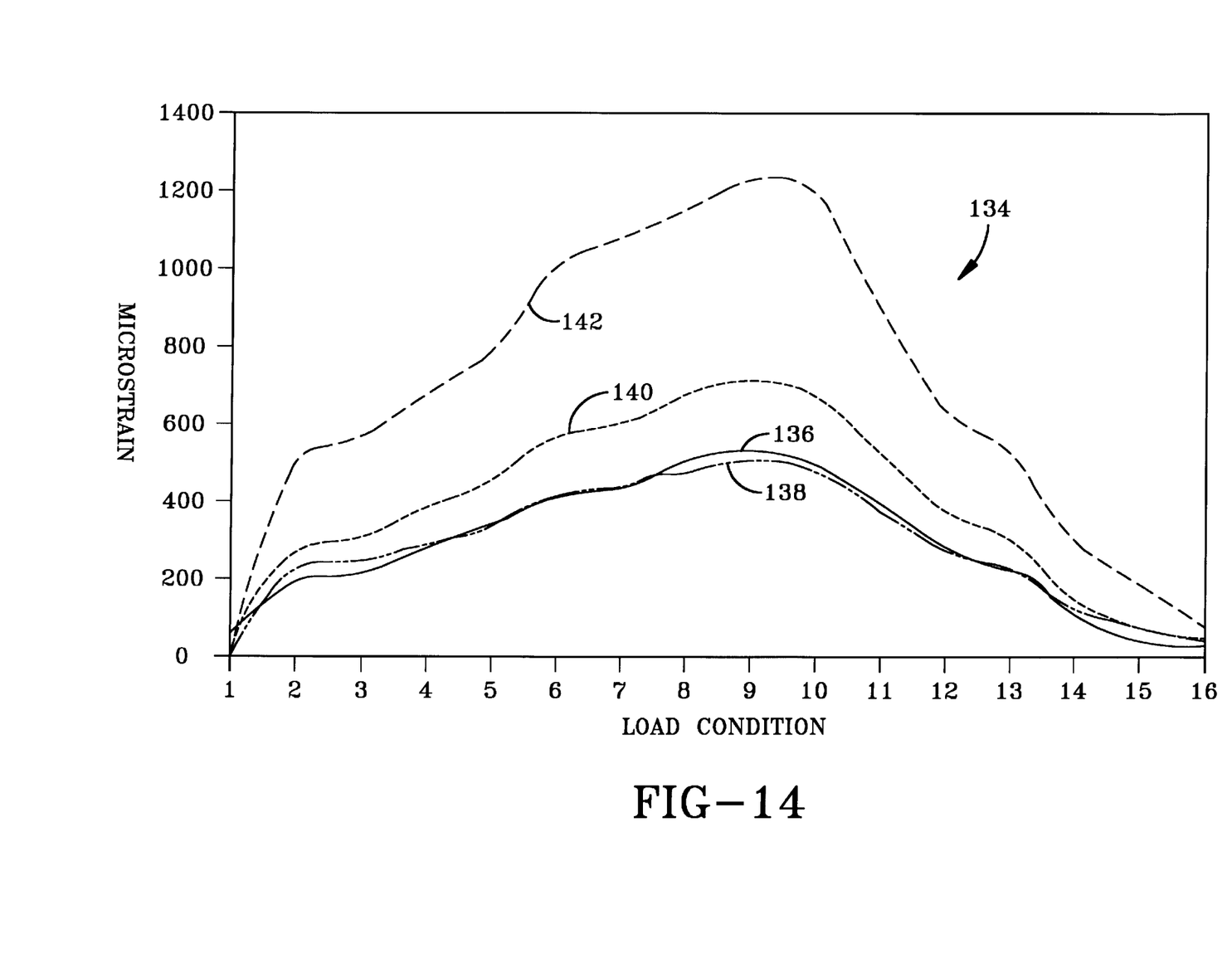
FIG. 14 illustrates pilot results obtained from the practice of the double-sensor extensometer configuration of the present invention mounted in an acrylic specimen, with surface-mounted strain gage output plotted as a comparison.

In the practice of the invention, testing was performed using the double-sensor extensometer 22 of FIG. 2 and the results 134 are shown in FIG. 14 represented by plots 136, 138, 140 and 142. FIG. 14 illustrates pilot results obtained from a double-sensor extensometer 22 mounted in an acrylic specimen, with a surface-mounted strain gage output plotted as a comparison. FIG. 14 has a Y axis indicated in microstrain ($\mu\epsilon$), and an X axis indicated by load condition 0N-25N-0N (where N=Newtons). The positive-slope and negative-slope regions of each of the plots 136, 138, 140 and 142 along the X-axis of FIG. 14 respectively represent loading and unloading conditions. The specimen was subjected to cantilevered bending.

Plot 136 represents the predicted strain at the surface obtained from the double-sensor extensometer 22, such as at the surface of the calcaneus 14 of FIG. 1(A). Plot 138 represents the measured strain at the surface obtained with a surface-mounted metal-foil strain gage known in the art. Plot 140 represents the measured strain at the double-sensor extensometer's 22 inboard sensors, that is the one closest to the specimen surface. Plot 142 represents the measured strain at the double-sensor extensometer's 22 outboard sensor, that is the one furthest away from the specimen surface.

From the pilot study summarized by FIG. 14, in particular from plots 136 and 138, it is seen that the practice of the present invention provides measurement of the strains which occur in planes which do not contain sensors. This technique could be used to estimate strains occurring within a specimen, such as bone.

It is understood that the invention is not limited to the specific embodiments herein illustrated and described but may be otherwise without departing from the spirit and scope of the invention. Although the capacitive delta extensometer has been described for use to provide in vivo measurements of bone strain, it should be recognized that strain measurements in other materials, for example, porous metals, plastic and ceramics, where surfaces with high porosity make it impractical to use surface-mounted strain gauges are contemplated by the practice of the present invention.

It should now be appreciated that the practice of the present invention provides various embodiments of capacitive sensors that can measure the in vivo strain encountered by the bone of a mammal, such as a human being.

What I claim is:

1. A capacitive extensometer adapted to be inserted into the bone of a mammal system for sensing the in vivo strain of said bone, said extensometer comprising:

(a) three pins adapted to be inserted into said bone; and (b) six (6) capacitive sensors mounted across said three pins and each providing a variable capacitance whose value is varied by the strain to which said bone is subjected, wherein said six (6) capacitive sensors are grouped into pairs with each pair being arranged on a five (5) sided member having a sensor face along which said pair is attached and spaced apart from each other.

2. The capacitive extensometer according to claim 1, wherein there are three five (5) sided members which are arranged so that three pins are each positioned at an apex of an equivalent triangle.

3. The capacitive extensometer according to claim 1, wherein said six (6) sensors are grouped into three pairs with each of the three pairs attached to said sensor face of three respective five-sided members and each of the attached pair is oriented 120 degrees from each other.

4. The capacitive extensometer according to claim 3, wherein each of said six (6) sensors generates an electrical signal.

5. The capacitive extensometer according to claim 4, wherein each electric signal is received by a serial arrangement comprising an amplifier and analog-to-digital converter.

6. The capacitive extensometer according to claim 5, wherein said serial arrangement further comprises a linearizing circuit and a low pass filter interposed between said amplifier and said analog-to-digital converter.

7. The capacitive extensometer according to claim 6, wherein said electrical signal after passing through said serial arrangement is delivered to a processor.

* * * * *